United States Patent

Nishioka et al.

Patent Number: 5,024,108
Date of Patent: Jun. 18, 1991

[54] SAMPLE ANALYZER

[75] Inventors: Yasuyuki Nishioka, Nagaokakyo; Akihiro Hirano, Kyoto, both of Japan

[73] Assignee: Horiba, Ltd., Kyoto, Japan

[21] Appl. No.: 458,091

[22] Filed: Dec. 28, 1989

[30] Foreign Application Priority Data

Jan. 14, 1989 [JP] Japan ................................. 1-2975

[51] Int. Cl.⁵ ............................................. G01N 1/22
[52] U.S. Cl. .................................. 73/863.11; 73/23.2; 73/863.31; 73/864.62; 436/181
[58] Field of Search ........... 73/863.11, 863.12, 864.17, 73/864.62, 864.21, 863, 863.33, 863.31, 863.32, 23.2, 25.03; 250/338.1, 338.5, 343, 288 R; 422/80, 83, 90, 91, 93, 98, 119; 436/174, 181

[56] References Cited

U.S. PATENT DOCUMENTS

| 944,247 | 12/1909 | Smith | 73/23.2 X |
|---|---|---|---|
| 3,359,784 | 12/1967 | Jorre et al. | 73/23.2 |
| 3,457,787 | 7/1969 | Maatsch et al. | 73/863.31 X |
| 3,520,657 | 7/1970 | Frumerman | 73/23.2 X |
| 4,128,008 | 12/1978 | Linenberg | 73/863.12 |
| 4,153,415 | 5/1979 | Espitalie et al. | 436/155 X |
| 4,298,026 | 11/1981 | Ambers | 422/63 X |
| 4,414,857 | 11/1983 | Brazhnikov et al. | 73/863.11 |
| 4,676,656 | 6/1987 | Cook et al. | 73/863.91 X |

FOREIGN PATENT DOCUMENTS

| 839725 | 5/1952 | Fed. Rep. of Germany ... 73/864.62 |
|---|---|---|
| 1188836 | 3/1965 | Fed. Rep. of Germany ... 73/863.11 |

*Primary Examiner*—Tom Noland
*Attorney, Agent, or Firm*—Price Gess & Ubell

[57] ABSTRACT

A sample analyzer to detect elements in a gaseous residue generated in an extraction furnace. The sample analyzer introduces the gaseous residue into a detector to be analyzed. The sample analyzer employs a buffer vessel having a variable internal capacity disposed between the extraction furnace and the detector. The variable capacity buffer vessel provides the capability to accurately analyze samples having wide variations in the concentration of substances to be analyzed.

5 Claims, 1 Drawing Sheet

SAMPLE ANALYZER

BACKGROUND OF THE INVENTION

1. Field of the Invention

The present invention relates to a sample analyzer in which a gas from an extraction furnace is introduced into a detector to be analyzed.

2. Description of Related Art

One of the conventional uses for sample analyzers is for analyzing oxygen and nitrogen contained in a sample such as metal. A sample analyzer may be used to analyze a sample such as oxide ceramics and nitride ceramics containing a relatively large amount of oxygen and nitrogen therein, the so-called high-concentration samples. A buffer vessel, for suppressing a momentary concentration of gases ($Co$, $N_2$) generated in an extraction furnace, must be used between the extraction furnace and the detector. In cases where a low-concentration sample, such as iron or steel, containing a relatively small amount of oxygen and nitrogen, or ceramics containing a small amount of oxygen and nitrogen as impurities is analyzed, the buffer vessel must be removed.

It is labor intensive to install and remove the buffer vessel each time the analytical sample is switched from a high-concentration sample to a low-concentration sample. Moreover, time is required for the detector to stabilize each time the buffer vessel is installed or removed. The result is that the analysis takes a long time. In cases where a high-concentration and a low-concentration come at random, the inconvenience is compounded and use of the analyzer becomes particularly difficult.

OBJECTS AND SUMMARY OF THE INVENTION

It is an object of the present invention to provide a sample analyzer capable of executing an appointed analysis within a short time. This is accomplished by eliminating the above-described problems.

In order to achieve the above-described object, a sample analyzer according to the present invention utilizes a buffer vessel which has a changeable internal capacity. This specialized buffer vessel is disposed between the extraction furnace and a detector.

With this construction, the analysis can be performed simply by reducing the internal capacity of the buffer vessel when a low-concentration sample is analyzed and increasing the internal capacity of the buffer vessel when a high-concentration sample is analyzed. Since only the internal capacity of the buffer vessel is changed, it is unnecessary to install and remove the buffer vessel. Additionally, it takes very little time for the detector to stabilize, so that the entire time period required for the analysis is reduced. Furthermore, the analysis can be continuously executed from a low-concentration range to a high-concentration range by means of a single buffer vessel.

The features of the present invention which are believed to be novel are set forth with particularity in the appended claims. The present invention, both as to its organization and manner of operation, together with further objects and advantages thereof, may be best understood by reference to the following description, taken in conjunction with the accompanying drawings.

BRIEF DESCRIPTION OF THE DRAWINGS

The preferred embodiment of the present invention is shown in FIGS. 1 and 2, in which.

DESCRIPTION OF THE PREFERRED EMBODIMENTS

The following description is provided to enable any person skilled in the analyzer industry to make and use the invention and sets forth the best modes contemplated by the inventors of carrying out their invention. Various modifications, however, will remain readily apparent to those skilled in the arts, since the generic principles of the present invention have been defined herein specifically to provide a relatively easily manufactured analyzer assembly for analyzing samples from an extraction furnace.

Figure 1:
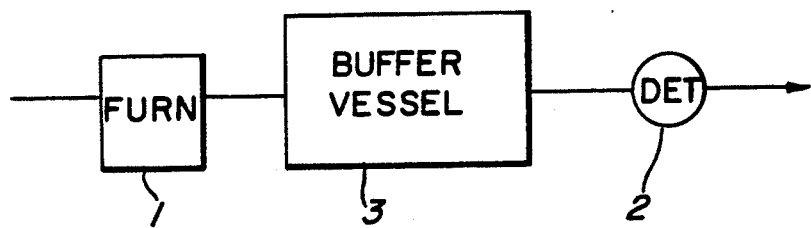
FIG. 1 is a block diagram showing a sample analyzer according to the present invention.

FIG. 1 shows one example of a sample analyzer according to the present invention. An extraction furnace 1 is provided having a pair of electrodes to electrify and thereby heat the sample. The sample is placed in a crucible, which is then placed in the furnace between heating electrodes (not shown). The electrodes are supplied with alternating current which heats the sample to the desired temperature.

Reference numeral 2 designates a detector provided in the analytical part of the system, for example, an infrared detector for detecting a concentration of oxygen.

Figure 2:
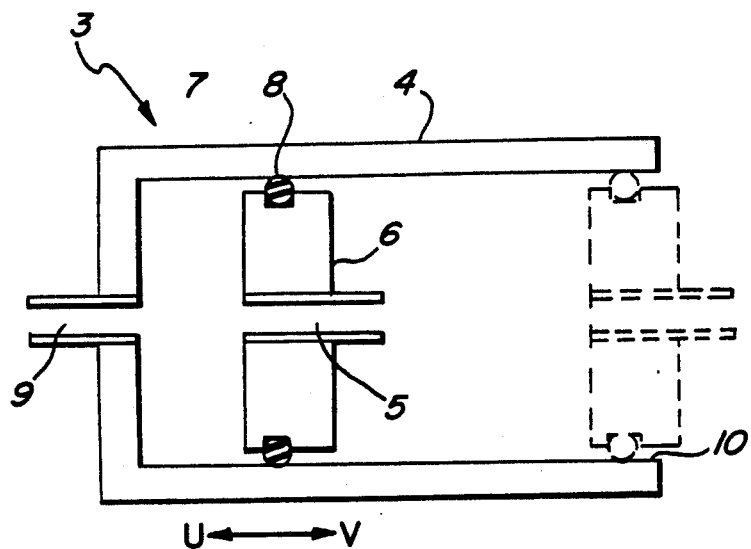
FIG. 2 is a sectional view showing one example of a buffer vessel according to the present invention.

Reference numeral 3 (FIG. 1) designates a buffer vessel disposed between the extraction furnace 1 and the detector 2. The buffer vessel 3 (FIG. 2) comprises a preferably cylindrical stationary vessel 4 with a piston 6 therein, having a gas passage 5. The piston is slideable in the direction of arrow U–V. The internal capacity of a chamber 7, connected with the extraction furnace 1, is thereby changeable by sliding the piston 6 in said direction by means of a driving mechanism (not shown).

A sealing member 8, such as an O-ring, is provided on the periphery of the piston 6. A gas inlet passage 9 communicates with the chamber 7. A gas outlet passage 5 is formed in the piston 6. The entire piston 6 and gas outlet are movable towards the detector 2 and the end of vessel 4.

The sample analyzer of the above-described construction is used as follows. In the case where a low-concentration sample is measured, the piston 6 is slid in the direction of the arrow U (FIG. 2) to reduce the internal capacity of the chamber 7. When a high-concentration sample is to be measured, the piston 6 is slid in the direction of the arrow V (FIG. 2) to increase the internal capacity of the chamber 7. In both instances, the required analysis can be accurately and quickly performed.

According to the above-described construction, even though the concentration of the sample turns out to actually be different from the expected concentration, the analysis can be carried out without interruption. For example, when the concentration of the sample is actually higher than expected, and the internal capacity of the chamber 7 is actually smaller than required, the piston 6 can be slid in the direction of the arrow V. This increases the internal capacity of chamber 7, so that the chamber's internal capacity corresponds to the actual situation. In particular, since the concentration range is wide in the analysis of new materials, an inconvenience in operation exists in the prior art. The present invention can quickly accommodate wide variations that exist in the concentration range of samples, therefore eliminating the inconvenience that previously existed.

Figure 3:
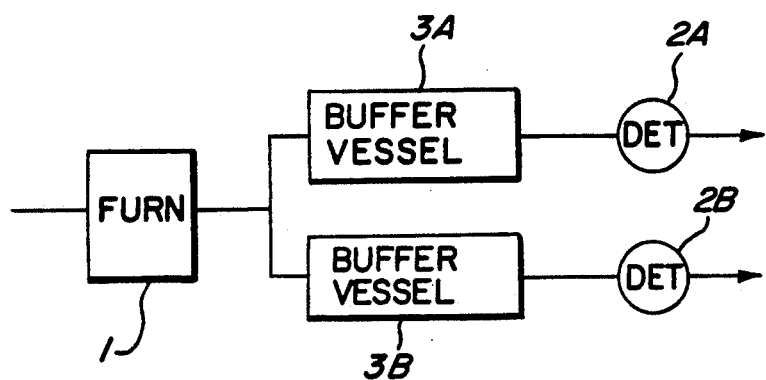
FIG. 3 is a block diagram showing an alternate preferred embodiment of the present invention.

FIG. 3 shows another preferred embodiment of the present invention in which oxygen and nitrogen can be independently and simultaneously analyzed. Referring to FIG. 3, reference numerals 3A, 3B designate buffer vessels having the same construction as the buffer vessel 3 (FIG. 2) in the above-described embodiment. These buffer vessels 3A, 3B are connected in parallel. In addition, reference numerals 2A, 2B designate detectors connected on the downstream side of the buffer vessels 3A, 3B, respectively. For example, the detector 2A is an infrared ray detector for detecting oxygen. Detector 2B is a thermal conductivity-type detector for detecting nitrogen.

With a sample analyzer having this construction, in a case where the concentration of oxygen in the sample is high and the concentration of nitrogen is low, or vice versa, or where both concentrations of oxygen and nitrogen are high (or low), the analysis can be accurately carried out by simply setting the internal capacities of the chambers in the buffer vessels 3A, 3B to match the respective expected concentration levels of oxygen and nitrogen.

In many cases, the content of oxygen in the sample is quite different from the content of nitrogen (for example). In the case where the sample is $Si_3N_4$, the content of nitrogen is 30% to 50% by weight, while the content of oxygen is 0.01% to 5% by weight. In such cases, it is necessary to optimize the capacity of the buffer for every ingredient to be measured. The present invention can sufficiently accommodate such widely different concentrations by means of the dual adjustable chambers.

According to the present invention as described above, the appointed analysis of not only the low-concentration sample, but also the high-concentration sample, can be carried out within a short time. The analysis can be accomplished without the extensive labor that would be required by the prior art. Additionally, according to the present invention, continuous analysis of a sample is possible, so that mass analysis is also possible.

What is claimed is:

1. A sample analyzer in which a gas from an extraction furnace is introduced into a detector to be analyzed, the improvement therein comprising a buffer vessel having a variable internal volume capacity disposed between said extraction furnace and said detector; whereby the volume of the buffer vessel may be adjusted as needed to accommodate a range of sample concentrations.

2. The sample analyzer of claim 1, wherein said buffer vessel comprises:
   a cylindrical stationary vessel; and
   a piston provided with a gas passage therein adapted to slidably move within said cylindrical stationary vessel to increase or decrease the working volume of the buffer vessel.

3. The sample analyzer of claim 1 wherein said buffer vessel comprises a plurality of buffer vessels connected in parallel to the extraction furnace and to respective corresponding detectors.

4. A sample analyzer comprising
   an extraction furnace for heating the sample to be analyzed;
   a first detector for analyzing gaseous residues from said extraction furnace; and
   a first buffer vessel having an adjustable volume capacity disposed between said extraction furnace and said first detector, said buffer vessel including a piston inside the vessel capable of being moved to adjust the internal volume capacity of the vessel, said piston having an outlet passage to permit gas to flow from the vessel.

5. The sample analyzer of claim 4 further comprising:
   a second buffer vessel connected in parallel with the first buffer vessel to the extraction furnace; and
   a second detector for analyzing gaseous residue from the extraction furnace provided to the second detector by said second buffer vessel.

* * * * *